(12) United States Patent
Kinkade et al.

(10) Patent No.: US 10,172,308 B1
(45) Date of Patent: Jan. 8, 2019

(54) TETRAPLOID WATERMELON LINE 74WA002

(71) Applicant: Syngenta Participations AG, Basel (CH)

(72) Inventors: Matthew Kinkade, Woodland, CA (US); James P. Brusca, Davis, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/861,028

(22) Filed: Jan. 3, 2018

(51) Int. Cl.
*A01H 1/02* (2006.01)
*A01H 5/08* (2018.01)
*A01H 6/34* (2018.01)

(52) U.S. Cl.
CPC ................ *A01H 5/08* (2013.01); *A01H 1/02* (2013.01); *A01H 6/342* (2018.05)

(58) Field of Classification Search
CPC .................................. A01H 5/08; A01H 6/342
See application file for complete search history.

(56) References Cited

U.S. PATENT DOCUMENTS 9,066,478 B2 * 6/2015 Juarez ...................... A01H 1/02
9,402,357 B1 8/2016 Brusca

* cited by examiner

*Primary Examiner* — Lee A Visone
(74) *Attorney, Agent, or Firm* — Karen A. Magri

(57) ABSTRACT

The present invention provides novel watermelon line 74WA002 and plant parts, seed, and tissue culture therefrom. The invention also provides methods for producing a watermelon plant by crossing the watermelon plants of the invention with themselves or another watermelon plant. The invention also provides watermelon plants produced from such a crossing as well as plant parts, seed, and tissue culture therefrom. Further provided are methods of producing triploid watermelon seed and plants and seedless watermelon fruit produced therefrom as well as the triploid watermelon seed and plants and the seedless fruits produced by such methods.

26 Claims, No Drawings

TETRAPLOID WATERMELON LINE 74WA002

FIELD OF THE INVENTION

This invention is in the field of watermelon plants, in particular, the invention relates to a novel tetraploid watermelon line, which can be used to produce triploid seeds and plants for production of seedless watermelon fruit.

BACKGROUND OF THE INVENTION

This invention relates to a new and unique inbred tetraploid watermelon line, designated 74WA002.

Watermelon is an important horticultural crop that accounts for 2% of the world area devoted to vegetable crops. There were 3,810,535 hectares (Ha) of watermelon grown in the world, and 51,110 Ha of watermelons grown in the United States in 2009. Asia is by far the most important watermelon production site with 78% of the world area and 83.4% of the world production of 100,687,056 metric tons. The estimated annual world watermelon value exceeded $7.6 billion when using the United States average price for 1995-1997. Watermelon is grown in at least forty-four states in the United States, with Florida, Georgia, California, and Texas, having long warm growing seasons, being the major producing states. In the United States, watermelon production has increased from 1.2 M tons in 1980 to 3.8 M tons in 2009, with an annual farm value of $470 million (U. S. Department of Agriculture, Agricultural Statistics, 2009).

In recent years, there has been an increase in consumer demand for seedless watermelons, and production of seedless watermelon has increased significantly. Triploid seedless watermelons have been commercially grown in the United States since the late 1980's. Currently, over 80% of the watermelons produced in the United States are triploid seedless watermelons. Seedless watermelon receives well above the average price for seeded watermelons in the market. Triploid seedless watermelon also produces higher yields than the diploid seeded watermelons.

Triploid seedless watermelon is a true F1 hybrid between a tetraploid watermelon, as the female parent, and a diploid watermelon, as the male parent (Kihara, H. 1951, *Triploid Watermelons*, Proceedings of American Society for Horticultural Science, 58:217-230). Diploid watermelons have 22 chromosomes (2N=2X=22) in their somatic cells, and tetraploid watermelons have 44 chromosomes (2N=4X=44) in their somatic cells. Cells with three sets of homologous chromosomes are said to be triploid and are designated as 3X. When female flowers of tetraploid plants are cross pollinated by the male flowers of diploid plants, the fruits produced by the tetraploid plants contain triploid seeds that produce triploid plants. The triploid seedless watermelons have 33 chromosomes (2N=3X=33) in their somatic cells. When the triploid plants are grown with diploid plants in the same field, the triploid plants produce fruits that are seedless. The seedless condition in triploid watermelon is the result of the presence of three homologous sets of chromosome per somatic cell rather than the usual two. The inability of the triploid zygote to produce normal viable gametes (pollen and egg cells) causes the absence of seeds in triploid fruits. Typically, seedless watermelons contain small edible white ovules, similar to those in immature cucumbers.

Watermelon, in general, and seedless watermelon in particular, is an important and valuable vegetable crop. Thus, there is an ongoing need for improved inbred tetraploid watermelon lines.

SUMMARY OF THE INVENTION

According to the invention, there is provided a novel inbred tetraploid watermelon line designated 74WA002, characterized by small, round fruits having a dark green (sugar baby) skin color and yellow flesh, lower thousand seed weight as compared with comparison variety 4XDKFD55G, and resistances to *Fusarium* wilt race 1 and Anthracnose (*Colletotrichum orbiculare*) race 1. Thus, the invention also encompasses the seeds of watermelon line 74WA002, the plants of watermelon line 74WA002, plant parts of the watermelon line 74WA002 (including fruit, seed, gametes, rootstock, shoots), methods of producing seed from watermelon line 74WA002, and methods for producing a watermelon plant by crossing the watermelon line 74WA002 with itself or another watermelon plant, methods for producing a watermelon plant containing in its genetic material one or more transgenes, and the transgenic watermelon plants produced by that method. The invention also relates to methods for producing other watermelon plants derived from watermelon line 74WA002 and to watermelon plants, parts thereof and seed produced by the use of those methods. The present invention further relates to hybrid watermelon seeds and plants (and parts thereof including fruit) produced by crossing watermelon line 74WA002 with another watermelon plant, e.g., hybrid triploid seeds and plants produced by crossing with a diploid plant.

In another aspect, the present invention provides regenerable cells for use in tissue culture of watermelon line 74WA002. In embodiments, the tissue culture is capable of regenerating plants having all or essentially all of the physiological and morphological characteristics of the foregoing watermelon plant and/or of regenerating plants having the same or substantially the same genotype as the foregoing watermelon plant. In embodiments, the regenerated plant is a tetraploid plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, the present invention provides watermelon plants regenerated from the tissue cultures of the invention.

As a further aspect, the invention provides a method of producing watermelon seed, the method comprising crossing a plant of watermelon line 74WA002 with itself or a second watermelon plant and allowing seed to form (e.g., tetraploid or triploid hybrid seed). Optionally, the method further comprises collecting the seed.

Another aspect of the invention provides methods for producing hybrids and other watermelon plants derived from watermelon line 74WA002. Watermelon plants derived by the use of these methods are also part of the invention as well as plant parts, seed, gametes and tissue culture from such hybrid or derived watermelon plants.

In representative embodiments, a watermelon plant derived from watermelon line 74WA002 comprises cells comprising at least one set of chromosomes derived from watermelon line 74WA002. In embodiments, the derived watermelon plant is a tetraploid plant. In embodiments, the derived watermelon plant is a triploid plant. In embodiments, the derived watermelon plant is a diploid plant.

In embodiments, a watermelon plant or population of watermelon plants derived from watermelon line 74WA002 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from watermelon line 74WA002, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 74WA002, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the derived watermelon plant is a tetraploid plant. In embodiments, the derived watermelon plant is a triploid plant. In embodiments, the derived watermelon plant is a diploid plant. In embodiments, the watermelon plant derived from watermelon line 74WA002 is one, two, three, four, five or more breeding crosses removed from watermelon line 74WA002.

In embodiments, a hybrid or derived plant from watermelon line 74WA002 comprises a desired added trait(s). In representative embodiments, a watermelon plant derived from watermelon line 74WA002 comprises all of the morphological and physiological characteristics of watermelon line 74WA002 (e.g., as described in Tables 1-2). In embodiments, the watermelon plant derived from watermelon line 74WA002 comprises essentially all of the morphological and physiological characteristics of watermelon line 74WA002 (e.g., as described herein), with the addition of a desired added trait(s). In embodiments, the plant derived from line 74WA002 is a tetraploid plant. In embodiments, the plant derived from line 74WA002 is a triploid plant. In embodiments, the plant derived from line 74WA002 is a diploid plant.

The invention also relates to methods for producing a watermelon plant comprising in its genetic material one or more transgenes and to the transgenic watermelon plant produced by those methods (and progeny watermelon plants comprising the transgene). Also provided are plant parts, seed and tissue culture from such transgenic watermelon plants, optionally wherein one or more cells in the plant part, seed, or tissue culture comprises the transgene. The transgene can be introduced via plant transformation and/or breeding techniques.

In another aspect, the present invention provides for single gene converted plants of watermelon line 74WA002. Plant parts, seed, and tissue culture from such single gene converted plants are also contemplated by the present invention. The single transferred gene may be a dominant or recessive allele. In representative embodiments, the single transferred gene confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single gene may be a naturally occurring watermelon gene or a transgene introduced into watermelon through genetic engineering techniques.

The invention further provides methods for developing watermelon plants (e.g., diploid, triploid or tetraploid) in a watermelon plant breeding program using plant breeding techniques including, for example, recurrent selection, backcrossing, pedigree breeding, double haploid techniques, restriction fragment length polymorphism enhanced selection, genetic marker enhanced selection and/or transformation. Seeds, watermelon plants, and parts thereof, produced by such breeding methods are also part of the invention.

The invention also provides methods of multiplication or propagation of watermelon plants of the invention, which can be accomplished using any method known in the art, for example, via vegetative propagation and/or seed.

Additional aspects of the invention include harvested products and processed products from the watermelon plants of the invention. A harvested product can be a whole plant or any plant part, as described herein. Thus, in some embodiments, a non-limiting example of a harvested product includes a seed, a fruit (e.g., including the flesh and/or rind), a rootstock and/or a shoot.

In representative embodiments, a processed product includes, but is not limited to: cut, sliced, ground, pureed, dried, canned, jarred, washed, packaged, frozen and/or heated fruit (including the fruit flesh and/or rind) of the watermelon plants of the invention, or any other part thereof. In embodiments, a processed product includes a sugar or other carbohydrate, fiber, protein and/or aromatic compound that is extracted, purified or isolated from a watermelon plant of the invention. In embodiments, the processed product includes washed and sliced fruit (or parts thereof, e.g., the fruit flesh with or without the rind) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of watermelon line 74WA002.

As a further aspect, the invention provides a plant of watermelon line 74WA002.

As an additional aspect, the invention provides a watermelon plant, or a part thereof, having all or essentially all of the physiological and morphological characteristics of a plant of watermelon line 74WA002. Optionally, the plant having all or essentially all of the physiological and morphological characteristics of a plant of watermelon line 74WA002 is a tetraploid plant.

The invention also provides plants that are diploid reversions of tetraploid watermelon line 74WA002 and parts (including seed and fruits) thereof. Also provided are methods of producing a diploid reversion derived from watermelon line 74WA002.

Also provided are methods of producing a diploid reversion of tetraploid watermelon plant of the invention. In embodiments, the method comprises crossing two plants of watermelon line 74WA002 or selfing watermelon line 74WA002, harvesting seed, and growing a diploid reversion from the harvested seed. In embodiments, the fruit and/or seed of the diploid reversion is collected. Optionally, the diploid reversion can be used in a watermelon breeding program. For example, the diploid reversion can be crossed with itself or another diploid watermelon plant to produce a further watermelon plant, fruit and seed derived from watermelon line 74WA002. In embodiments, the method further comprises doubling the chromosomes of the diploid reversion (or a diploid watermelon progeny thereof) to produce a tetraploid watermelon plant.

The invention further provides triploid watermelon seed and triploid watermelon plants (and parts thereof, such as seedless fruit) produced by crossing watermelon line 74WA002 with a diploid plant. Optionally, 74WA002 is used as the female parent.

As another aspect, the invention provides fruit and/or seed of the watermelon plants of the invention and a processed product from the fruit and/or seed of the inventive watermelon plants.

As still another aspect, the invention provides a method of producing watermelon seed, the method comprising crossing a watermelon plant of the invention with itself or a second watermelon plant. In embodiments, the method is practiced to produce seed of line 74WA002 (e.g., seed increase). The invention also provides seed produced by this method and plants, and parts thereof including fruit, produced by growing the seed.

As yet a further aspect, the invention provides a method for producing a seed of a watermelon plant derived from watermelon line 74WA002, the method comprising: (a) crossing a watermelon plant of watermelon line 74WA002 with a second watermelon plant; and (b) allowing seed of a watermelon plant derived from watermelon line 74WA002 to form. In embodiments, the method further comprises: (c) growing a plant from the seed derived from watermelon line 74WA002 of step (b); (d) selfing the plant of step (c) or crossing it to a second watermelon plant to form additional watermelon seed derived from watermelon line 74WA002, and (e) optionally repeating steps (c) and (d) one or more times to generate further derived watermelon seed from watermelon line 74WA002, wherein in step (c) a plant is grown from the additional watermelon seed of step (d) in place of growing a plant from the seed of step (b). In embodiments, the method comprises: (e) repeating steps (c) and (d) one or more times (e.g., one to three, one to five, one to six, one to seven, one to ten, three to five, three to six, three to seven, three to eight or three to ten times) to generate further derived watermelon seed. As another option, the method can comprise collecting the seed. The invention also provides seed produced by these methods and watermelon plants (e.g., tetraploid watermelon plants) produced by growing the seed.

Still further, as another aspect, the invention provides a method of vegetatively propagating a plant of watermelon line 74WA002, e.g., via shoot proliferation and then rooting in tissue culture. Detailed methods were described by Zhang et al. (Zhang, X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae' 94: 134-139). In a non-limiting example, the method comprises: (a) collecting tissue capable of being propagated from a plant of watermelon line 74WA002; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into watermelon line 74WA002, the method comprising: (a) crossing a first plant of watermelon line 74WA002 with a second watermelon plant that comprises a desired trait to produce $F_1$ progeny; (b) selecting an $F_1$ progeny that comprises the desired trait; (c) crossing the selected $F_1$ progeny with watermelon line 74WA002 to produce backcross progeny; and (d) selecting backcross progeny comprising the desired trait to produce a plant derived from watermelon line 74WA002 comprising a desired trait.

In embodiments, the selected progeny produces a small fruit. In embodiments, the selected progeny produces a round fruit. In embodiments, the selected progeny produces a fruit having a dark green (e.g., sugar baby) skin. In embodiments, the selected progeny produces a fruit with yellow flesh. In embodiments, the selected progeny produces seed with a lower thousand seed weight as compared with comparison variety 4XDKFD55G. In embodiments, the selected progeny has resistance to *Fusarium* wilt race 1 and/or Anthracnose race 1. In embodiments, the selected progeny comprises all or essentially all the morphological and physiological characteristics of watermelon line 74WA002 (e.g., a described in Tables 1-2). Optionally, the method further comprises: (e) repeating steps (c) and (d) one or more times (e.g., one to three, one to five, one to six, one to seven, one to ten, three to five, three to six, three to seven, three to eight or three to ten times) to produce a plant derived from watermelon line 74WA002 comprising the desired trait, wherein in step (c) the selected backcross progeny produced in step (d) is used in place of the selected F1 progeny of step (b). In embodiments, the plant derived from line 74WA002 and comprising the desired added trait is a tetraploid plant. In embodiments, the plant derived from line 74WA002 and comprising the desired added trait is a triploid plant. In embodiments, the plant derived from line 74WA002 and comprising the desired added trait is a diploid plant.

In representative embodiments, the invention also provides a method of producing a plant of watermelon line 74WA002 comprising a desired added trait, the method comprising introducing a transgene conferring the desired trait into a plant of watermelon line 74WA002. The transgene can be introduced by transformation methods (e.g., genetic engineering) or breeding techniques. In embodiments, the plant comprising the transgene produces a small fruit. In embodiments, the plant comprising the transgene produces a round fruit. In embodiments, the plant comprising the transgene produces a fruit having a dark green (e.g., sugar baby) skin. In embodiments, the plant comprising the transgene produces a fruit with yellow flesh. In embodiments, the plant comprising the transgene produces seed with a lower thousand seed weight as compared with comparison variety 4XDKFD55G. In embodiments, the plant comprising the transgene has *Fusarium* wilt race 1 resistance and/or Anthracnose race 1, and optionally is a tetraploid plant. In embodiments, the plant comprising the transgene comprises all or essentially all of the morphological and physiological characteristics of watermelon line 74WA002 (e.g., as described in Tables 1-2).

The invention also provides watermelon plants (e.g., a tetraploid watermelon plant) produced by the methods of the invention, wherein the watermelon plant has the desired added trait as well as seed and fruits from such watermelon plants. The invention also provides seed that produces the plants derived from line 74WA002 and comprising a desired added trait.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, transformed plants (e.g., using genetic engineering techniques), single gene converted plants, hybrid plants and watermelon plants derived from watermelon line 74WA002 are characterized by, e.g., one or more of tetraploidy, small fruits, round fruits, fruits having a dark green (e.g., sugar baby) skin color, fruits having yellow flesh, fruits having a relatively low thousand seed weight, and/or resistance to *Fusarium* wilt race 1 and/or Anthracnose race 1. In representative embodiments, transgenic plants, transformed plants, hybrid plants and watermelon plants derived from watermelon line 74WA002 have at least 3, 4, 5, 6, 7, 8, 9, 10 or more of the morphological and physiological characteristics of watermelon line 74WA002 (for example, tetraploidy, small, round fruits having a dark green (e.g., sugar baby) skin color and yellow flesh, relatively low thousand seed weight, and/or resistance to *Fusarium* wilt race 1 and/or Anthracnose race 1, e.g., as described in Tables 1 and 2), or even all of the morphological and physiological characteristics of watermelon line 74WA002, so that said plants are not significantly different for said traits than watermelon line 74WA002, as determined at the 5% significance level when grown in the same environmental conditions; optionally, with the presence of one or more desired additional traits (e.g., male sterility, disease resistance, pest or insect resistance, herbicide resistance, and the like).

As a further aspect, the invention provides a method of producing triploid watermelon seed, the method comprising: (a) crossing a watermelon plant of line 74WA002 with a diploid watermelon plant; and (b) optionally, harvesting the resultant triploid watermelon seed. In embodiments, the plant of line 74WA002 is the female parent and the diploid parent is the male plant (i.e., pollenator). Also provided is a hybrid triploid watermelon seed produced by the foregoing method, and a triploid watermelon plant (and parts thereof, including seedless fruit) grown from the triploid seed.

The invention also provides as another aspect, a method of producing seedless watermelon fruit, the method comprising: (a) crossing the triploid watermelon plant produced by the method of the preceding paragraph and a diploid watermelon plant; (b) allowing a seedless fruit to form; and (c) optionally, harvesting the seedless fruit. In embodiments, the plant of line 74WA002 is the female parent and the diploid parent is the male plant (i.e., pollenator). Also provided is a seedless watermelon fruit produced by the foregoing method.

As still a further aspect, the invention provides a tetraploid watermelon plant, or a part thereof, produced by crossing a 74WA002 plant with a different tetraploid watermelon plant (e.g., a tetraploid inbred or hybrid plant).

The invention further provides a method of developing a tetraploid watermelon line in a watermelon plant breeding program using plant breeding techniques, which include employing a watermelon plant, or a part thereof, as a source of plant breeding material, the method comprising: (a) obtaining the watermelon plant, or a part thereof, of line 74WA002 as a source of breeding material; and (b) applying plant breeding techniques.

The invention also encompasses plant parts, plant material, pollen, ovules, leaves, fruit and seed from the watermelon plants of the invention. The invention also provides seed that produces the watermelon plants of the invention. Also provided is a tissue culture of regenerable cells from the watermelon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are watermelon plants regenerated from a tissue culture of the invention.

In still yet another aspect, the invention provides a method of determining a genetic characteristic of watermelon line 74WA002 or a progeny thereof, e.g., a method of determining a genotype of watermelon line 74WA002 or a progeny thereof using molecular genetic techniques. In embodiments, the method comprises detecting in the genome of a 74WA002 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel watermelon characterized by production of small, round fruits having a dark green (e.g., sugar baby) skin color and yellow flesh, relatively low thousand seed weight, and by resistance to *Fusarium* wilt race 1 and Anthracnose race 1.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

Those skilled in the art will appreciate that when a comparison of physiological and morphological characteristics between two or more varieties is made, it is assumed that the varieties are grown under the same environmental conditions, whether in the field or green house. In addition, such comparisons are generally made on the basis of observations taken on a population of plants, which define the characteristics of the variety.

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotype of the $F_1$ hybrid.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all the physiological and morphological characteristics". A plant having "essentially all the physiological and morphological characteristics" means a plant having all of the desired physiological and morphological characteristics of variety 74WA002, e.g., when both plants are grown under the same environmental conditions. In embodiments, the plant comprising "essentially all of the physiological and morphological characteristics" of variety 74WA002 is tetraploid, comprises a small fruit size, a round fruit having a dark green (sugar baby) skin and yellow internal flesh, and is resistant to *Fusarium* race 1 and Anthracnose race 1 (e.g., when both plants are grown under the same environmental conditions), and is optionally diploid or tetraploid. In embodiments, a plant comprising "essentially all of the physiological and morphological characteristics" of variety 74WA002 comprises the traits of Tables 1 and 2.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing. In representative embodiments, the plant part is a non-propagating plant part, for example, is not a seed.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A watermelon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single gene converted". A single gene converted or conversion plant refers to a plant that is developed by plant breeding techniques (e.g., backcrossing) or via genetic engineering wherein essentially all of the desired morphological and physiological characteristics of a line are recovered in addition to the single gene transferred into the line via the plant breeding technique or via genetic engineering.

As used herein, a "small" watermelon fruit refers to a mean fruit weight that is less than about 8 kg, 7 kg, 6 kg, 5 kg, 4.5 kg or even 4 kg.

"Substantially equivalent characteristic". A characteristic that, when compared, does not show a statistically significant difference (e.g., p=0.05) from the mean.

"Thousand seed weight" as used herein refers to the average weight of 1000 seeds of the variety. In embodiments, the plant or variety has a "low" or "relatively low" thousand seed weight, e.g., less than about 55, 50, 45, 44, 43, 42, 41 or 40 grams per thousand seeds (e.g., untreated seeds).

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Tetraploid Watermelon Lines and Triploid Seed Production

The primary use of tetraploid watermelons is to make triploid hybrid watermelon seeds and plants that produce seedless fruit. In commercial production of triploid watermelon seed, tetraploid and diploid parental lines are typically planted in the same field. Cross-pollination between the tetraploid line, generally used as the female parental line, and the diploid line, the male parental line, are accomplished by either hand or bee pollination. Triploid watermelon seeds are produced only in fruits of tetraploid plants that are fertilized with pollen of diploid plants. All commercially grown seeded watermelons are diploid; therefore, there are many diploid lines for use as diploid parents. The major limitation to development of seedless watermelon varieties lies in the availability of useful elite tetraploid parental lines.

Tetraploid watermelon lines can be developed from diploid lines by doubling the chromosomes of diploid watermelon lines using methods routine in the art. Chromosome doubling was first accomplished with the alkaloid colchicine by applying colchicine to the growing point of newly emerged watermelon seedlings. Tissue culture methods have also been developed (Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139). Dinitroanilines have been used to double chromosome numbers, and their effectiveness has previously been compared with crops other than watermelon. Li et al. compared in vitro chromosome doubling effectiveness using colchicine and the dinitroanilines, ethalfluralin (N-ethyl-N-2-methyl-2-propenyl)-2,6-dinitro-4-(trifluoromethyl) benzanine), and oryzalin (3,5-dinitro-N4, N4-dipropylsulfanilamide) and concluded that either ethalfluralin or oryzalin was preferable to colchicine (Li, Ying, J. F. Whitesides, B. Rhodes, 1999, *In vitro generation of tetraploid watermelon with two different dinitroanilines and colchicines*, Cucurbit Genetics Cooperative Rpt 22:38-40).

Several treatment methods can be used to induce tetraploids from diploids using the chemicals mentioned above. One exemplary method is to treat the seed before sowing. The seed are soaked in clean water for 5-6 hrs and then the seed are soaked in either colchicine solution (0.2%) or dinitroanilines (e.g. 35 µM oryzalin) for 24 hrs. The seed are briefly rinsed before sowing. Dry seed can also be directly soaked in the chemical solution without pre-soaking in the water. The treatment usually reduces the germination and emergence. A second method is to treat the newly emerged seedling. To illustrate, the diploid inbreds can be sown in the greenhouse in seedling flats. The soil temperature is kept at 29-31° C. for rapid and uniform germination. One drop of colchicine (0.1%) or dinitroanilines (e.g. 35 µM oryzalin) solution is added to the shoot apex between the cotyledons as soon as the seedling has emerged from soil. The colchicine solution is applied to the growing point in the morning or evening for three consecutive days. Good chromosome doubling is achieved from application of oryzalin. Another illustrative method is to treat the shoot apex of germinated seed after which the germinated seed is planted into soil. The seeds are germinated in an incubator at 30° C. When the radicals are about 2 cm long, the portion above the hypocotyls of germinated seeds is immersed upside down into colchicine (0.1%) or dinitroaniline solution (35 µM oryzalin) for 10-15 hrs at 30° C. in an incubator. The treatment is typically conducted in a high humidity chamber or box to assure that the radicals/roots are not desiccated. The seeds are then washed and planted in the soil. The last two methods, although more tedious to use, usually give better recovery of tetraploid events as the root system is not affected by the treatment.

The next step is to develop tetraploid lines from individual converting events. For example, the selected tetraploid individuals based on morphological expression can be self-pollinated and the resulting seeds planted in the next generation as lines. These lines can again be self-pollinated and compared for fertility and horticultural traits. Only the desirable lines are selected if there is difference among these lines. Desirable lines may be bulk harvested if there is no variation within the line and among selected lines. Further seed increases may be conducted in an isolation block. Mass selection may be conducted for this increase in the isolation plot and thereafter. Fertility of the tetraploid may be improved in subsequent generations.

The use of tissue culture to propagate tetraploid watermelon plants is exemplified in Adelberg, J. W., B. B. Rhodes, *Micropropagation from zygotic tissue of watermelon*, C. E. Thomas (ed.) Proc. of the Cucurbitaceae 89: Evaluation and enhancement of cucurbit germplasm, Charleston S.C., USA; and Zhang et al., *Shoot regeneration from immature cotyledon of watermelon*, Cucurbit Genetics Coop. 17:111-115 (1994).

Crossing two different tetraploids and then going through recombination breeding can also result in new tetraploid lines. A longer breeding period is typically employed to develop a stable tetraploid line using this approach because of the larger number of combinations and the fewer seed that tetraploids produce. However, some breeders have made good progress by taking this approach.

Because meiosis is sometimes irregular in autotetraploids, there can be diploids and aneuploids among the offspring. The leaves, flowers and pollen grains of tetraploids are morphologically distinct from diploids (Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139). Tetraploids also have a different number of chloroplasts in the guard cells (Compton, M. E., D. J. Gray and G. W. Elmstrom. 1996, *Identification of tetraploid regenerants from cotyledons of diploid watermelon cultures in vitro*, Euphytica 87:165-172). These morphological traits can help the breeder eliminate the diploids and aneuploids occurring in the tetraploid population during sexual propagation. Diploid reversions can also be identified in situations in which a diploid derived from line 74WA002 is desired, and such diploid reversions are also encompassed by the present invention.

Several methods can be used to produce triploid seeds from an inbred tetraploid line. Two commonly used methods are the bee-pollination method and the hand-pollination method. In the United States, the bee-pollination method is generally used to produce triploid watermelon seed. Hand-pollination is mainly used to produce triploid watermelon seed in areas where isolation is not available and several triploid hybrids are produced in the same field block.

Botanical Description of the Watermelon Line 74WA002.

Characteristics. Watermelon inbred tetraploid line 74WA002 is characterized by producing fruits having a round shape, dark (sugar baby) skin color, yellow internal flesh color, and resistance to *Fusarium* wilt race 1 and Anthracnose race 1.

Test crosses of triploid hybrids produced using 74WA002 as female parent have been evaluated. Promising triploid hybrids have been selected for multiple location trials. 74WA002 is a new, unique and useful elite inbred tetraploid line for producing triploid seedless hybrids.

Watermelon line 74WA002 has shown uniformity and stability within the limits of environmental influence. It has been self-pollinated for numerous generations with careful attention to uniformity of plant type. The variety has been increased with continued observation for uniformity. No variant traits have been observed or are expected in watermelon line 74WA002.

New watermelon tetraploid variety 74WA002 is unique in that it combines the following traits: fruits having a round shape, dark (sugar baby) skin color, yellow internal flesh color, and resistance to *Fusarium* wilt race 1. Line 4XDKFD55G (U.S. Pat. No. 9,402,357) was selected as the most similar variety because it is a tetraploid line with resistance to *Fusarium* wilt race 1, round fruit shape, and a fruit size similar to 74WA002. However, 74WA002 is distinguishable because it has a dark green (sugar baby) skin color and yellow internal flesh color, whereas 4XDKFD55G has a grey skin color and red flesh. 74WA002 has also a lower thousand seed weight as compared with 4XDKFD55G (37.54 grams per 1000 seeds versus 82.2 grams per thousand seeds, respectively).

A more detailed botanical description of 74WA002 and comparison with 90-4232 is shown in Table 1 below.

TABLE 1

Description of 74WA002 and comparison with 4XDKFD55G based on open field trials in Naples, Florida (2014, 2016) and Woodland, California (2016).

| Characteristic: | 74WA002 | 4XDKFD55G |
|---|---|---|
| General fruit type: | round large | round large |
| Area of best adaptation: | most areas | most areas |
| Maturity - No. of days from emergence of anthesis: | 15.2 days | 14.4 days |
| Maturity - No. of days from pollination to maturity: | 48.4 days | 47.7 days |
| Relative maturity: | 66 days | 63 days |
| Maturity category: | early | early |
| Ploidy: | tetraploid | tetraploid |
| Cotyledon shape: | flat | flat |
| Plant sex form: | monoecious | monoecious |
| Number of Main Stems at crown: | 2.6 | 3.4 |
| Number of flowers per plant at first fruit set: | 7.4 staminate, 2 pistillate, 0 perfect | 8.3 staminate, 1.9 pistillate, 0 perfect |
| Stem: | round, pubescent, 6.4 mm diameter at second node | round, pubescent, 6.6 mm diameter at second node |
| Vine length at last harvest: | 508 cm | 471.4 cm |
| No. internodes at last harvest: | 45.8 | 38.4 |
| Ratio cm vine length/internodes at last harvest: | 11.1 | 12.3 |
| Leaf shape: | ovate | ovate |
| Leaf lobes: | lobed | lobed |
| Leaf length: | 33.8 cm | 28.5 cm |
| Leaf width: | 23.3 cm | 22 cm |
| Leaf dorsal surface pubescence: | smooth | smooth |
| Leaf ventral surface pubescence: | smooth | smooth |
| Leaf color: | medium green | medium green |
| Flower: | staminate 4.05 cm across, pistillate 3.7 cm across, yellow (RHS 7D) | staminate 4.1 cm across, pistillate 3.65 cm across, yellow (RHS 7D) |
| Mature fruit: | round, 19.1 cm long, 18.9 cm diameter at midsection, 3.82 kg average weight, 5.3 kg maximum weight, smooth surface, dark green (sugar baby) skin color with a Jubilee stripe | round, 21.8 cm long, 21.7 cm diameter at midsection, 5.13 kg average weight, 7.7 kg maximum weight, smooth surface, solid skin color, light green (Charleston Grey) |
| Rind: | tough, 5 mm thick at blossom end, 14 mm thick at sides | tough, 7 mm thick at blossom end, 11 mm thick at sides |
| Flesh: | crisp, fine with little fiber, yellow, 11.1% soluble solids of juice at center of fruit (refractometer), no hollow heart, no placental separation, and no transverse cracking observed | crisp, fine with little fiber, red, 11% soluble solids of juice at center of fruit (refractometer), no hollow heart, no placental separation, and no transverse cracking observed |
| Seed (F1 seed; no seed in F1 fruit): | medium, 8.1 mm long, 5.9 mm wide, 1.9 mm | medium, 9.8 mm long, 6.7 mm wide, 1.8 mm |

TABLE 1-continued

Description of 74WA002 and comparison with
4XDKFD55G based on open field trials in Naples, Florida
(2014, 2016) and Woodland, California (2016).

|  | | |
|---|---|---|
|  | thick, index is 14 (length ÷ width × 10), 37.65 gm per 1000 seeds, 85.5 seeds per fruit, tan mottled color | thick, index is 14.7 (length ÷ width × 10), 82.2 gm per 1000 seeds, 81.6 seeds per fruit, dark brown mottled color |
| Anthracnose, Race 1: | resistant | resistant |
| *Fusarium* Wilt, Race 1: | resistant | resistant |

74WA002 is unique in that it combines dark (sugar baby) skin color, yellow internal flesh color, and resistance to *Fusarium* wilt race 1, conferred by the gene Fo-1 (Henderson, W. R., S. F. Jenkins, Jr., and J. O. Rawlings. 1970. The inheritance of *Fusarium* wilt resistance in watermelon, *Citrullus lanatus* (Thunb.) Mansf. J. Amer. Soc. Hort. Sci. 95: 276-282). As demonstrated in the standard pathology test results shown in Table 2 below, Black Diamond does not carry the resistance allele at the Fo-1 locus and is susceptible to *Fusarium* wilt race 1, whereas 74WA002 carries the resistance allele at the Fo-1 locus and is resistant to *Fusarium* wilt race 1.

TABLE 2

Test of Resistance to *Fusarium* wilt race 1 in 74WA002 and controls.

| Variety | Species | Isolate Used | Total Plant Inoc-ulated | R | S | % R | Results |
|---|---|---|---|---|---|---|---|
| 74WA002 | *Citrullus lanatus* var. *lanatus* | Race 1 (811B) | 17 | 15 | 2 | 88.2 | Resistant |
| SP-6 | *Citrullus lanatus* var. *lanatus* | Race 1 (811B) | 16 | 16 | 0 | 100.0 | Resistant |
| Black Diamond | *Citrullus lanatus* var. *lanatus* | Race 1 (811B) | 20 | 2 | 18 | 10.0 | Susceptible |

Standard *Fusarium* wilt resistant test protocol was used for this test. The test was conducted in the pathology greenhouse of the Woodland (California) station.
"R" = resistant plants,
"S" = susceptible plants.

Tissue Culture.

In embodiments, watermelon plants can be propagated by tissue culture and regeneration. Tissue culture of various plant tissues and regeneration of plants therefrom is well known. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a high rate of success. Thus, another aspect of this invention is to provide cells which upon growth and differentiation produce watermelon plants having desired characteristics of watermelon line 74WA002 (e.g., one or more of tetraploidy, small fruits, round fruits, fruits having a dark green (e.g., sugar baby) skin color, fruits having yellow flesh, relatively low thousand seed weight and/or by resistance to *Fusarium* wilt race 1 and/or Anthracnose race 1. Optionally, watermelon plants can be regenerated from the tissue culture of the invention comprising all or essentially all of the physiological and morphological characteristics of watermelon line 74WA002.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Production of Triploid Seed.

An important use of tetraploid watermelon is to make triploid hybrid watermelon seeds and plants that produce seedless fruit. The tetraploid line is optionally used as female parent to cross with a diploid watermelon line, generally the male parent line. The creation of a commercially desirable triploid hybrid generally relies on the performance (e.g., seed production) and the combining ability of the tetraploid parent.

Accordingly, the invention contemplates as one aspect a method of producing triploid watermelon seed, the method comprising: (a) crossing the watermelon plant of line 74WA002 with a diploid watermelon plant; and (b) harvesting the resultant triploid watermelon seed. In embodiments the plant of line 74WA002 is the female parent and the diploid plant is the male parent. In embodiments, the plant of line 74WA002 is the male parent and the diploid plant is the female parent. The triploid watermelon seed produces a triploid plant, which when grown into a plant produces a seedless watermelon fruit (i.e., when crossed with a diploid plant).

The invention further provides a method of producing seedless watermelon fruit, the method comprising: (a) crossing a triploid plant produced from line 74WA002 (e.g., an F1 hybrid of 74WA002 produced as described in the preceding paragraph) and a diploid watermelon plant; (b) allowing seedless fruit to form; and (c) optionally, harvesting the seedless fruit. In embodiments, the triploid watermelon seed and seed from a diploid plant are planted in one or more rows, and the plants are allowed to mature and develop seedless fruit. In embodiments, diploid and triploid seed are planted in the same row. In embodiments the triploid plant is the female parent and the diploid plant is the male parent. In embodiments, the triploid plant is the male parent and the diploid plant is the female parent.

Several methods can be used to produce triploid seeds from inbred 74WA002. Two commonly used methods are described below. Variations to these methods can be made according to the actual production situation.

Hand-Pollination Method

Hand pollination can be used for producing triploid seed from 74WA002. For example, in embodiments, the inbred tetraploid female parent 74WA002 and the inbred diploid male parent line are planted in the same field. To illustrate, in an exemplary method, the inbred male parent is planted 7-10 days earlier than the female parent 74WA002 to insure adequate pollen supply at the pollination time. The male parent and female parent 74WA002 can be planted, for example, in the ratio of 1 male parent to 4-10 female parents.

Optionally, the diploid male parent is planted at the top of the field for efficient male flower collection during pollination. Pollination is generally started when the second female flower on the tetraploid female parent 74WA002 is ready to flower. Female flower buds that are ready to open the next day are identified, covered with paper cups or small paper bags that prevent bee or any other insect visit of the female flowers, and marked with any kind of material that can be easily seen the next morning. The male flowers of the diploid male parent are collected in the morning before they are open and visited by pollinating insects. The covered female flowers of the tetraploid female parent, which have opened, are uncovered and pollinated with the collected fresh male flowers of the diploid male parent, starting after the male flower sheds pollen. The pollinated female flowers are again covered after pollination to prevent bees and any other insect visits. The pollinated female flowers are also marked. Generally, only the marked fruits are harvested for extracting triploid hybrid seed.

Bee-Pollination Method

Bee pollination can also be used in triploid watermelon production. In an exemplary bee-pollination method, the tetraploid female parent 74WA002 and the diploid male parent are typically planted in a ratio of 2 rows tetraploid parent to 1 row male parent. The female tetraploid plants are pruned to 2-3 branches. All of the male flower buds on the female tetraploid parent plants are removed manually (the de-budding process) during the pollination season, typically on a daily basis. Beehives are placed in the field for transfer of pollen by bees from the male parent to the female flowers of the female parent. Fruits set during this de-budding time are marked. Generally, only the marked fruits are harvested for extracting hybrid triploid seed.

Additional Breeding Methods.

This invention is also directed to methods for producing a watermelon plant by crossing a first parent watermelon plant with a second parent watermelon plant wherein the first or second parent watermelon plant is a plant of watermelon line 74WA002. Further, both first and second parent watermelon can come from watermelon line 74WA002. Thus, any of the following exemplary methods using watermelon line 74WA002 are part of this invention: selfing, backcrosses, hybrid production, crosses to populations, double haploid production, and the like. All plants produced using watermelon line 74WA002 as at least one parent are within the scope of this invention, including those developed from watermelon plants derived from watermelon line 74WA002. Advantageously, watermelon line 74WA002 can be used in crosses with other, different, watermelon plants to produce first generation ($F_1$) watermelon hybrid seeds and plants with desirable characteristics. The watermelon plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with watermelon line 74WA002 in the development of further watermelon plants. One such embodiment is a method for developing watermelon line 74WA002 progeny watermelon plants in a watermelon plant breeding program comprising: obtaining a plant, or a part thereof, of watermelon line 74WA002, utilizing said plant or plant part as a source of breeding material, and selecting a watermelon line 74WA002 progeny plant with molecular markers in common with watermelon line 74WA002 and/or with some, all or essentially all morphological and/or physiological characteristics of watermelon line 74WA002 (see, e.g., Tables 1-2). In representative embodiments, the progeny plant has at least 1, 2, 3, 4, 5, 6, 7, 8, 9, 10 or more of the morphological and physiological characteristics of watermelon line 74WA002 (for example, one or more of tetraploidy, small fruits, round fruits, fruits having a dark green (e.g., sugar baby) skin color, fruits having yellow flesh, relatively low thousand seed weight and/or by resistance to *Fusarium* wilt race 1 and/or Anthracnose race 1, e.g., as described in Tables 1 and 2), or even all of the morphological and physiological characteristics of watermelon line 74WA002 so that said progeny watermelon plant is not significantly different for said traits than watermelon line 74WA002, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of watermelon line 74WA002 progeny plants, comprising crossing watermelon line 74WA002 with another watermelon plant, thereby producing a population of watermelon plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 74WA002, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 74WA002. One embodiment of this invention is the watermelon plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 74WA002, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology.

One of ordinary skill in the art of plant breeding would know how to evaluate the traits of two plant varieties to determine if there is or is not significant difference between the two traits expressed by those varieties. For example, see Fehr and Walt, Principles of Cultivar Development, pp. 261-286 (1987). Thus, the invention includes watermelon line 74WA002 progeny watermelon plants characterized by e.g., one or more of tetraploidy, small fruits, round fruits, fruits having a dark green (e.g., sugar baby) skin color, fruits having yellow flesh, relatively low thousand seed weight and/or by resistance to *Fusarium* wilt race 1 and/or Anthracnose race 1. In embodiments, the invention encompasses progeny plants having a combination of at least 2, 3, 4, 5, 6, 7, 8, 9, 10 or more of the characteristics as described herein for watermelon line 74WA002, so that said progeny watermelon plant is not significantly different for said traits than watermelon line 74WA002, as determined at the 5% significance level when grown in the same environmental conditions. Using techniques described herein and those known in the art, molecular markers may be used to identify said progeny plant as progeny of watermelon line 74WA002. Mean trait values may be used to determine whether trait differences are significant, and optionally the traits are measured on plants grown under the same environmental conditions.

Progeny of watermelon line 74WA002 may also be characterized through their filial relationship with watermelon line 74WA002, as for example, being within a certain number of breeding crosses of watermelon line 74WA002. A breeding cross is a cross made to introduce new genetics into the progeny, and is distinguished from a cross, such as a self or a sib cross or a backcross to 74WA002 as a recurrent parent, made to select among existing genetic alleles. The lower the number of breeding crosses in the pedigree, the closer the relationship between watermelon line 74WA002 and its progeny. For example, progeny produced by the methods described herein may be within 1, 2, 3, 4, 5 or more breeding crosses of watermelon line 74WA002.

In representative embodiments, a watermelon plant derived from watermelon line 74WA002 comprises cells comprising at least one set of chromosomes derived from watermelon line 74WA002. In embodiments, the watermelon plant or population of watermelon plants derived from watermelon line 74WA002 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 74WA002, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 74WA002, and optionally may be the result of one or more of selfing, sibbing, backcrossing and/or double haploid techniques in any combination. In embodiments, the watermelon plant derived from watermelon line 74WA002 is one, two, three, four, five or more breeding crosses removed from watermelon line 74WA002.

In representative embodiments, a plant derived from watermelon line 74WA002 is a double haploid plant, a hybrid plant, an inbred plant, a tetraploid plant, a triploid plant and/or a diploid plant.

In embodiments, a derived plant from watermelon line 74WA002 comprises a desired added trait. In representative embodiments, a watermelon plant derived from watermelon line 74WA002 comprises all of the morphological and physiological characteristics of watermelon line 74WA002 (e.g., as described in Tables 1-2). In embodiments, the watermelon plant derived from watermelon line 74WA002 comprises essentially all of the morphological and physiological characteristics of watermelon line 74WA002 (e.g., as described herein), with the addition of a desired added trait.

According to the invention, tetraploid inbreds can be used as parental lines to develop new tetraploid lines. The unique and desirable traits of 74WA002 make it useful as a parental line in the development of new tetraploid inbreds. 74WA002 can be used as either female or male parent to cross with another tetraploid watermelon (e.g., and inbred or hybrid tetraploid) to develop new tetraploid inbreds.

Those skilled in the art will appreciate that any of the traits described herein with respect to plant transformation methods can be introduced into a plant of the invention (e.g., watermelon line 74WA002 and hybrid watermelon plants and other watermelon plants derived therefrom) using breeding techniques.

Further Embodiments of the Invention

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species or from the same species, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of watermelon plants disclosed herein.

Genetic engineering techniques can be used (alone or in combination with breeding methods) to introduce one or more desired added traits into plant, for example, watermelon line 74WA002 or progeny or watermelon plants derived thereof.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed watermelon plants using transformation methods as described herein to incorporate transgenes into the genetic material of the watermelon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

One commonly used selectable marker for plant transformation is a neomycin phosphotransferase II (nptII) coding sequence, for example, isolated from transposon Tn5, which when placed under the control of plant regulatory signals confers resistance to kanamycin. Fraley, et al., PNAS, 80:4803 (1983). Another commonly used selectable marker is hygromycin phosphotransferase, which confers resistance to the antibiotic hygromycin. Vanden Elzen, et al., Plant Mol. Biol., 5:299 (1985).

Additional selectable markers of bacterial origin that confer resistance to antibiotics include gentamycin acetyl transferase, streptomycin phosphotransferase, aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable markers confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Selectable markers for plant transformation that are not of bacterial origin include, for example, mouse dihydrofolate reductase, plant 5-enolpyruvylshikimate-3-phosphate synthase, and plant acetolactate synthase. Eichholtz, et al., Somatic Cell Mol. Genet., 13:67 (1987); Shah, et al., Science, 233:478 (1986); and Charest, et al., Plant Cell Rep., 8:643 (1990).

Another class of selectable marker for plant transformation involves screening of presumptively transformed plant cells rather than direct genetic selection of transformed cells for resistance to a toxic substance such as an antibiotic. These selectable markers are particularly useful to quantify or visualize the spatial pattern of expression of a transgene in specific tissues and are frequently referred to as a reporter gene because they can be fused to transgene or regulatory sequence for the investigation of nucleic acid expression. Commonly used reporters for screening presumptively transformed cells include alpha-glucuronidase (GUS), alpha-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., J. Cell Biol., 115:151a (1991).

Green Fluorescent Protein (GFP) is also utilized as a marker for nucleic acid expression in prokaryotic and eukaryotic cells. Chalfie, et al., Science, 263:802 (1994). GFP and mutants of GFP may be used as screenable markers.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a nucleic acid for expression in a plant. Optionally, the inducible promoter is operably linked to a nucleotide sequence encoding a signal sequence which is operably linked to a nucleic acid for expression in the plant. With an inducible promoter, the rate of transcription increases in response to an inducing agent.

Any inducible promoter can be used in the instant invention. See Ward, et al., Plant Mol. Biol., 22:361-366 (1993). Exemplary inducible promoters include, but are not limited to, that from the ACEI system which responds to copper (Melt, et al., PNAS, 90:4567-4571 (1993)); promoter from the In2 gene from maize which responds to benzenesulfonamide herbicide safeners (Hershey, et al., Mol. Gen. Genet., 227:229-237 (1991) and Gatz, et al., Mol. Gen. Genet., 243:32-38 (1994)) or Tet repressor from Tn10 (Gatz, et al., Mol. Gen. Genet., 227:229-237 (1991)). A representative inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., PNAS, 88:0421 (1991).

B. Constitutive Promoters:

A constitutive promoter is operably linked to a nucleic acid for expression in a plant or the constitutive promoter is operably linked to a nucleotide sequence encoding a signal sequence which is operably linked to a nucleic acid for expression in a plant.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a nucleic acid for expression in a plant. Optionally, the tissue-specific promoter is operably linked to a nucleotide sequence encoding a signal sequence which is operably linked to a nucleic acid for expression in a plant. Plants transformed with a nucleic acid of interest operably linked to a tissue-specific promoter transcribe the nucleic acid of interest exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

According to a representative embodiment, the transgenic plant provided for commercial production of foreign protein is a watermelon plant of the invention. In another embodiment, the biomass of interest is seed. For the relatively small number of transgenic plants that show higher levels of expression, a genetic map can be generated, for example via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR, and sequencing, all of which are conventional techniques.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those categorized below:

A. Transgenes that Confer Resistance to Pests or Disease:

1. Plant disease resistance transgenes. Plant defenses are often activated by specific interaction between the product of a disease resistance gene (R) in the plant and the product of a corresponding avirulence (Avr) gene in the pathogen. A plant line can be transformed with a cloned resistance transgene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt delta-endotoxin gene. Moreover, DNA molecules encoding delta-endotoxin transgenes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin transgenes.

4. A vitamin-binding protein such as avidin. See, e.g., PCT Application No. US 93/06487. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of *Streptomyces nitrosporeus* alpha-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266,317 to Tomalski, et al., who disclose transgenes encoding insect-specific, paralytic neurotoxins.

8. An insect-specific venom produced in nature, by a snake, a wasp, etc. For example, see Pang, et al, Gene, 116:165 (1992), for disclosure of heterologous expression in plants of a transgene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase transgene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin transgene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance).

13. A membrane permease, a channel former, or a channel blocker. For example, see the disclosure of Jaynes, et al., Plant Sci., 89:43 (1993), of heterologous expression of a cecropin-beta, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein transgene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody transgenes are protected from virus attack.

17. A developmental-arrestive protein produced in nature by a pathogen or a parasite. Thus, fungal endo-alpha-1,4-D-polygalacturonases facilitate fungal colonization and plant nutrient released by solubilizing plant cell wall homoalpha-1,4-D-galacturonase. See Lamb, et al., Bio/technology, 10:1436 (1992). The cloning and characterization of a transgene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating transgene have an increased resistance to fungal disease.

19. A watermelon mosaic potyvirus (LMV) coat protein transgene introduced into *Lactuca sativa* in order to increase its resistance to LMV infection. See Dinant, et al., Mol. Breeding, 3:1, 75-86 (1997).

Any disease or present resistance transgenes, including those exemplified above, can be introduced into a watermelon plant of the invention through a variety of means including but not limited to transformation and breeding.

B. Transgenes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) transgene, including but not limited to those described in U.S. Pat. Nos. 4,940,935, 5,188,642, 5,633,435, 6,566,587, 7,674,598 as well as all related application; or the glyphosate N-acetyltransferase (GAT) transgene, described in Castle et al., Science, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g., aryloxy alkanoate dioxygenase or AAD-1, AAD-12, or AAD-13), HPPD resistance (e.g., *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone,); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121, 512; 5,349,127; 6,649,814; and 6,300,544; and PCT International Publication No. WO 2007/000077); dicamba resistance (e.g., dicamba monoxygenase), and traits desirable for processing or process products such as high oil (e.g., U.S. Pat. No. 6,232,529); modified oils (e.g., fatty acid desaturase transgenes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., J. Bacteriol., 1988, 170:5837-5847) facilitate expression of polyhydroxyalkanoates (PHAs)).

In embodiments, the polynucleotide encodes a polypeptide conferring resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

Any transgene conferring herbicide resistance, including those exemplified above, can be introduced into the watermelon plants of the invention through a variety of means including, but not limited to, transformation (e.g., genetic engineering techniques) and crossing.

C. Transgenes that Confer or Contribute to a Value-Added Trait:

1. Increased iron content of the watermelon, for example, by introducing into a plant a soybean ferritin transgene as described in Goto, et al., *Acta Horticulturae.*, 521, 101-109 (2000).

2. Decreased nitrate content of leaves, for example, by introducing into a watermelon a transgene coding for a nitrate reductase. See, for example, Curtis, et al., *Plant Cell Rep.*, 18:11, 889-896 (1999).

3. Increased sweetness of the watermelon by introducing a transgene coding for monellin that elicits a flavor 100,000 times sweeter than sugar on a molar basis. See Penarrubia, et al., *Bio/technology,* 10:561-564 (1992).

4. Modified fatty acid metabolism, for example, by introducing into a plant an antisense sequence directed against stearyl-ACP desaturase to increase stearic acid content of the plant. See Knultzon, et al., PNAS, 89:2625 (1992).

5. Modified carbohydrate composition effected, for example, by introducing into plants a transgene coding for an enzyme that alters the branching pattern of starch. See Shiroza, et al., J. Bacteria, 170:810 (1988) (nucleotide sequence of *Streptococcus* mutants fructosyltransferase transgene); Steinmetz, et al., Mol. Gen. Genet., 20:220 (1985) (nucleotide sequence of *Bacillus subtilis* levansucrase transgene); Pen, et al., Bio/technology, 10:292 (1992) (production of transgenic plants that express *Bacillus lichenifonnis* alpha-amylase); Elliot, et al., Plant Mol. Biol., 21:515 (1993) (nucleotide sequences of tomato invertase transgenes); Sogaard, et al., J. Biol. Chem., 268:22480 (1993) (site-directed mutagenesis of barley alpha-amylase transgene); and Fisher, et al., Plant Physiol., 102:1045 (1993) (maize endosperm starch branching enzyme II).

Any transgene that confers or contributes a value-added trait, including those exemplified above, can be introduced into the watermelon plants of the invention through a variety of means including, but not limited to, transformation (e.g., genetic engineering techniques) and crossing.

D. Transgenes that Control Male-Sterility:

1. Introduction of a deacetylase transgene under the control of a tapetum-specific promoter and with the application of the chemical N-Ac-PPT. See, e.g., International Publication WO 01/29237.

2. Introduction of various stamen-specific promoters. See, e.g., International Publications WO 92/13956 and WO 92/13957.

3. Introduction of the barnase and the barstar transgenes. See, e.g., Paul, et al., Plant Mol. Biol., 19:611-622 (1992).

Any transgene that controls male sterility, including those exemplified above, can be introduced into the watermelon plants of the invention through a variety of means including, but not limited to, transformation (e.g., genetic engineering techniques) and crossing.

Methods for Plant Transformation.

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993).

A. *Agrobacterium*-Mediated Transformation.

One method for introducing an expression vector into plants is based on the natural transformation system of *Agrobacterium*. See, for example, Horsch, et al., Science, 227:1229 (1985); Curtis, et al., Journal of Experimental Botany, 45:279, 1441-1449 (1994); Torres, et al., Plant Cell Tissue and Organ Culture, 34:3, 279-285 (1993); and Dinant, et al., Molecular Breeding, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated transgene transfer are provided by Gruber, et al., supra, Miki, et al., supra, and Moloney, et al., Plant Cell Rep., 8:238 (1989). See also, U.S. Pat. No. 5,591,616 issued Jan. 7, 1997.

B. Direct Transgene Transfer.

Several methods of plant transformation collectively referred to as direct transgene transfer have been developed as an alternative to *Agrobacterium*-mediated transformation. A generally applicable method of plant transformation is microprojectile-mediated transformation wherein DNA is carried on the surface of microprojectiles measuring 1 micron to 4 micron. The expression vector is introduced into plant tissues with a biolistic device that accelerates the microprojectiles to speeds of 300 m/s to 600 m/s which is sufficient to penetrate plant cell walls and membranes. Russell, D. R., et al., Plant Cell Rep., 12 (3, January), 165-169 (1993); Aragao, F. J. L., et al., Plant Mol. Biol., 20 (2, October), 357-359 (1992); Aragao, F. J. L., et al., Plant Cell Rep., 12 (9, July), 483-490 (1993); Aragao, Theor. Appl. Genet., 93:142-150 (1996); Kim, J., Minamikawa, T., Plant Sci., 117:131-138 (1996); Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol. Plant, 7:206 (1990); Klein, et al., Bio/technology, 10:268 (1992).

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985) and Christou, et al., PNAS, 84:3962 (1987). Direct uptake of DNA into protoplasts using CaCl.sub.2 precipitation, polyvinyl alcohol, or poly-L-ornithine has also been reported. Hain, et al., Mol. Gen. Genet., 199:161 (1985) and Draper, et al., Plant Cell Physiol., 23:451 (1982). Electroporation of protoplasts and whole cells and tissues have also been described. Saker, M., Kuhne, T., Biologia Plantarum, 40(4):507-514 (1997/98); Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., Plant Mol. Biol., 24:51-61 (1994). See also Chupean, et al., Bio/technology, 7:5, 503-508 (1989).

Following transformation of plant target tissues, expression of the above-described selectable marker transgenes allows for preferential selection of transformed cells, tissues and/or plants, using regeneration and selection methods now well known in the art.

The foregoing methods for transformation would typically be used for producing a transgenic watermelon line. The transgenic watermelon line could then be crossed with another (non-transformed or transformed) line in order to produce a new transgenic watermelon line. Alternatively, a genetic trait that has been engineered into a particular plant cultivar using the foregoing transformation techniques could be introduced into another line using traditional breeding (e.g., backcrossing) techniques that are well known in the plant breeding arts. For example, a backcrossing approach could be used to move an engineered trait from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Gene Conversions.

When the term "watermelon plant" is used in the context of the present invention, this term also includes any gene conversions of that plant or variety. The term "gene converted plant" as used herein refers to those watermelon plants that are developed, for example, by backcrossing, genetic engineering and/or mutation, wherein essentially all of the desired morphological and physiological characteristics of a variety (e.g., tetraploidy, small fruits, round fruits, fruits having a dark green (e.g., sugar baby) skin color, fruits having yellow flesh, relatively low thousand seed weight and/or by resistance to *Fusarium* wilt race 1 and/or Anthracnose race 1) are recovered in addition to the one or more genes transferred into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, pest or disease resistance (e.g., resistance to bacterial, fungal, or viral disease), insect resistance, enhanced nutritional quality, increased sweetness, increased flavor, improved ripening control, improved salt tolerance, industrial usage, yield stability, and yield enhancement. These genes are generally inherited through the nucleus.

Genetic Analysis of Watermelon Line 74WA002.

The invention further provides a method of determining a genetic characteristic of watermelon line 74WA002 or a progeny thereof, e.g., a method of determining a genotype of watermelon line 74WA002 or a progeny thereof. In embodiments, the method comprises detecting in the genome of a 74WA002 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

Deposit Information

Applicants have made a deposit of at least 2500 seeds of watermelon line 74WA002 with the American Type Culture Collection (ATCC), 10801 University Boulevard, Manassas, Va., 20110-2209 U.S.A. under ATCC Deposit No PTA-125110 on May 11, 2018. This deposit of watermelon variety 74WA002 will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant inbred and the like may be practiced within the scope of the invention.

What is claimed is:

1. A seed of tetraploid watermelon 74WA002, a representative sample of seed having been deposited under ATCC Accession No. PTA-125110.

2. A plant of tetraploid watermelon 74WA002, a representative sample of seed having been deposited under ATCC Accession No. PTA-125110.

3. A watermelon plant, or a part thereof, having all the physiological and morphological characteristics of the watermelon plant of claim 2.

4. A seed that produces the plant of claim 3.

5. A plant part of the plant of claim 2, wherein the plant part is a fruit, an F1 seed, a shoot, pollen, an ovule, an anther, a root, or a cell.

6. A tissue culture of regenerable cells of the watermelon plant of claim 2.

7. A method of producing watermelon seed, the method comprising crossing the plant of claim 2 with itself or a second watermelon plant and harvesting the resulting seed.

8. An F1 seed produced by the method of claim 7.

9. A watermelon plant, or a fruit thereof, produced by growing the seed of claim 8.

10. A method of producing a watermelon plant, the method comprising growing a diploid reversion of a watermelon plant produced by growing the watermelon seed of claim 7.

11. The method according to claim 10, further comprising the step of doubling the chromosome number of said diploid reversion to produce a tetraploid watermelon plant.

12. A method of developing a watermelon line in a watermelon plant breeding program using plant breeding techniques, which include employing a watermelon plant, or its parts, as a source of plant breeding material, comprising:
    (a) obtaining the watermelon plant, or its parts, of claim 2 as a source of breeding material; and
    (b) applying plant breeding techniques.

13. A method for producing a seed of a watermelon plant derived from the plant of claim 2, the method comprising:
    (a) crossing a plant of watermelon line 74WA002 with a second watermelon plant; and
    (b) allowing seed to form;
    (c) growing a plant from the seed of step (b) to produce a plant derived from watermelon line 74WA002;
    (d) selfing the plant of step (c) or crossing it to a second watermelon plant to form additional watermelon seed derived from watermelon line 74WA002; and
    (e) optionally repeating steps (c) and (d) one or more times to generate further derived watermelon seed from watermelon line 74WA002, wherein in step (c) a plant is grown from the additional watermelon seed of step (d) in place of growing a plant from the seed of step (b).

14. A method of vegetatively propagating the plant of claim 2, the method comprising:
    (a) collecting tissue capable of being propagated from a plant of watermelon line 74WA002;
    (b) cultivating the tissue to obtain proliferated shoots;
    (c) rooting the proliferated shoots to obtain rooted plantlets; and
    (d) optionally, growing plants from the rooted plantlets.

15. A method of introducing a desired added trait into watermelon line 74WA002, the method comprising:
    (a) crossing the plant of claim 2 with a watermelon plant that comprises a desired added trait to produce F1 progeny;
    (b) selecting an F1 progeny that comprises the desired added trait;
    (c) crossing the selected F1 progeny with watermelon line 74WA002 to produce backcross progeny;
    (d) selecting a backcross progeny comprising the desired added trait and otherwise all of the physiological and morphological characteristics of the watermelon line 74WA002; and
    (e) optionally repeating steps (c) and (d) one or more times to produce a plant derived from watermelon line 74WA002 comprising a desired added trait and otherwise all of the physiological and morphological characteristics of watermelon line 74WA002, wherein in step (c) the selected backcross progeny produced in step (d) is used in place of the selected F1 progeny of step (b).

16. A watermelon plant produced by the method of claim 15 or a selfed progeny thereof, wherein said watermelon plant or selfed progeny thereof has the desired added trait and otherwise has all of the physiological and morphological characteristics of watermelon line 74WA002.

17. A seed that produces the plant of claim 16.

18. A method of producing a plant of watermelon line 74WA002 comprising a desired added trait, the method comprising introducing a transgene conferring the desired trait into the plant of claim 2.

19. A watermelon plant produced by the method of claim 18 or a selfed progeny thereof, wherein said watermelon plant or selfed progeny thereof comprises the transgene and has the desired added trait and otherwise has all of the physiological and morphological characteristics of watermelon line 74WA002.

20. A seed that produces the plant of claim 19.

21. A method of producing triploid watermelon seed, the method comprising:
    (a) crossing the watermelon plant of claim 2 with a diploid watermelon plant; and
    (b) harvesting the resultant triploid watermelon seed.

22. An F1 triploid watermelon seed produced by the method of claim 21.

23. An F1 triploid watermelon plant, or fruit thereof, produced from the seed of claim 22.

24. A method of producing seedless watermelon fruit, the method comprising:
    (a) crossing the triploid plant of claim 23 and a diploid watermelon plant;
    (b) allowing seedless fruit to form; and
    (c) harvesting the seedless fruit.

25. A method of producing a tetraploid watermelon plant, the method comprising crossing the plant of claim 2 with a different tetraploid watermelon plant.

26. An F1 tetraploid watermelon plant, or a fruit thereof, produced by the method of claim 25.

* * * * *